(12) United States Patent
Giles et al.

(10) Patent No.: US 9,466,473 B2
(45) Date of Patent: Oct. 11, 2016

(54) COAXIAL ION GUIDE

(71) Applicant: Micromass UK Limited, Wilmslow (GB)

(72) Inventors: Kevin Giles, Stockport (GB); Martin Raymond Green, Bowdon (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/774,473

(22) PCT Filed: Mar. 13, 2014

(86) PCT No.: PCT/GB2014/050748
§ 371 (c)(1),
(2) Date: Sep. 10, 2015

(87) PCT Pub. No.: WO2014/140579
PCT Pub. Date: Sep. 18, 2014

(65) Prior Publication Data
US 2016/0042935 A1 Feb. 11, 2016

(30) Foreign Application Priority Data

Mar. 13, 2013 (EP) .................................... 13159069
Mar. 13, 2013 (GB) .................................. 1304521.6

(51) Int. Cl.
| *H01J 49/36* | (2006.01) |
| *H01J 49/42* | (2006.01) |
| *H01J 49/06* | (2006.01) |
(Continued)

(52) U.S. Cl.
CPC ........... *H01J 49/065* (2013.01); *G01N 27/622* (2013.01); *H01J 49/0031* (2013.01); *H01J 49/427* (2013.01); *H01J 49/4265* (2013.01)

(58) Field of Classification Search
CPC . G01N 27/622; G01N 27/624; H01J 49/066; H01J 49/004; H01J 49/065; H01J 49/36; H01J 49/0031; H01J 49/06; H01J 49/42; H01J 49/4225; H01J 49/424; H01J 49/426; H01J 49/4265; H01J 49/427
USPC ....... 250/281, 282, 288, 291, 283, 290, 292, 250/293, 396 R
See application file for complete search history.

(56) References Cited

U.S. PATENT DOCUMENTS

| 6,107,628 A | 8/2000 | Smith et al. |
| 6,727,495 B2 | 4/2004 | Li |
| 6,979,816 B2 | 12/2005 | Tang et al. |

(Continued)

FOREIGN PATENT DOCUMENTS

| CN | 101369510 | 2/2009 |
| WO | 0063949 | 10/2000 |

(Continued)

*Primary Examiner* — David A Vanore
(74) *Attorney, Agent, or Firm* — Diederiks & Whitelaw, PLC

(57) ABSTRACT

A method of mass and/or ion mobility spectrometry is disclosed comprising: trapping ions in an annular or co-axial ion trap; and then axially ejecting at least some of said ions from said annular or co-axial ion trap into an annular ion guide. Ions trapped in the ion trap are distributed around the entire circumference of the annular or co-axial ion trap. As the ions travel along at least a portion of the length of the ion guide their motion around the circumference of the annular ion guide is unrestricted and the ions separate axially as they travel along the ion guide.

20 Claims, 6 Drawing Sheets

(51) Int. Cl.
  *G01N 27/62* (2006.01)
  *H01J 49/00* (2006.01)

(56) References Cited

U.S. PATENT DOCUMENTS

| | | | |
|---|---|---|---|
| 7,170,053 B2 | 1/2007 | Shvartsburg et al. | |
| 7,652,270 B2 * | 1/2010 | Dzengeleski | H01J 37/1477 250/396 ML |
| 7,653,841 B2 | 1/2010 | Yokokura | |
| 7,851,752 B2 * | 12/2010 | Kim | H01J 49/066 250/292 |
| 8,410,432 B2 | 4/2013 | Miller et al. | |
| 8,507,852 B2 * | 8/2013 | Makarov | G01N 27/622 250/281 |
| 8,698,075 B2 | 4/2014 | Kurulugama et al. | |
| 9,070,543 B2 * | 6/2015 | Green | G01N 27/624 |
| 9,082,604 B2 | 7/2015 | Verenchikov | |
| 9,343,285 B2 * | 5/2016 | Green | H01J 49/065 |
| 2004/0195503 A1 * | 10/2004 | Kim | H01J 49/066 250/288 |
| 2009/0001265 A1 * | 1/2009 | Baba | G01N 27/622 250/288 |
| 2012/0153140 A1 * | 6/2012 | Makarov | G01N 27/622 250/282 |
| 2015/0233866 A1 | 8/2015 | Verenchikov | |
| 2016/0042935 A1 * | 2/2016 | Giles | G01N 27/622 250/283 |

FOREIGN PATENT DOCUMENTS

| | | |
|---|---|---|
| WO | 2013/005058 | 1/2013 |
| WO | 2013/050747 | 4/2013 |

* cited by examiner

COAXIAL ION GUIDE

CROSS-REFERENCE TO RELATED APPLICATION

This application is the National Stage of International Application No. PCT/GB2014/050748, filed 13 Mar. 2014 which claims priority from and the benefit of United Kingdom patent application No. 1304521.6 filed on 13 Mar. 2013 and European patent application No. 13159069.7 filed 13 Mar. 2013. The entire contents of these applications are incorporated herein by reference.

BACKGROUND OF THE PRESENT INVENTION

The present invention relates to a method of mass and/or ion mobility spectrometry and a mass and/or ion mobility spectrometer.

Ion mobility separators are known in which ions are separated according to their ion mobilities. In order to improve the duty cycle of ion mobility separation, the ions may be accumulated in a trapping region upstream of the ion mobility spectrometer or separator device. As all the ions are stored in this trapping region prior to release into the drift tube, the space charge capacity of this upstream trapping region can ultimately limit the performance of the ion mobility spectrometer or separator device. Excessive amounts of charge in the trapping region can lead to detrimental effects on performance of the downstream analyser. For example, if the charge capacity of the device is exceeded then ions may be lost from the trapping region. There may be undesirable mass and/or charge discrimination in the portion of the population of ions lost from the trapping region due to the nature of the confining force provided by the RF confinement field. In addition, there may be fragmentation of molecular ions as ions are pushed closer to the confining electrodes due to mutual space charge repulsion.

One way to increase the charge capacity is to extend the axial length of the trapping region. However, the resolution of the downstream ion mobility spectrometer or separator will be reduced if an axially extended ion packet is introduced into the ion mobility spectrometer or separator. Best performance is preferably achieved when the packet of ions introduced into the device has the minimum practical axial distribution prior to ion mobility separation.

Accordingly, it is desired to provide an improved mass spectrometer and method of mass spectrometry.

SUMMARY OF THE PRESENT INVENTION

According to a first aspect of the present invention there is provided a method of mass and/or ion mobility spectrometry comprising:

trapping ions in an annular or co-axial ion trap, wherein the trapped ions are distributed around the entire circumference of the annular or co-axial ion trap; and then axially ejecting at least some of said ions from said annular or co-axial ion trap into an annular ion guide, wherein the ions separate axially as they travel along the ion guide, and wherein as the ions travel along at least a portion of the length of the ion guide their motion around the circumference of the annular ion guide is unrestricted; and then converting the ions from an ion beam having an annular shaped cross section to an ion beam having a non-annular shaped cross-section.

As the present invention provides an annular or co-axial ion trap and an annular ion guide, the ion trapping volume and hence charge capacity is significantly increased over conventional devices, which generally have a substantially circular inside cross section. The trapping geometry of the present invention maximises the space charge capacity available and conditions the ion population into a volume which is suitable for direct injection into the coaxial ion guide.

US 2012/0153140 discloses an ion mobility spectrometer comprising an annular storage section arranged upstream of an annular drift tube. In operation, ions are pulsed from the storage section into the drift tube and the ions then separate as they pass through the drift tube. In a low resolution mode of operation, the ions are confined by electrodes within an arcuate section of the drift tube as they travel towards the exit of the drift tube. However, this known device suffers from a number of disadvantages. For example, as the ions are confined within the arcuate section as the travel along the drift tube, the ions suffer from space-charge effects. Also, ions in the annular storage section that do not pass into the arcuate section of the drift tube are not able to exit the device and will be lost.

According to US 2010/0153140, ions are extracted from the device by a potential difference between an annular conductive strip and an exit plate having an exit aperture. Ions further away from the exit plate experience a lower extraction field than ions near to the exit plate. As the extraction field decreases for ions that are more remote from the extraction plate, the time taken for ions of the same mobility to exit the device will be variable and may be longer than the ion mobility separation time scale and the temporal width of the ion mobility peak exiting the device. The device will therefore have a poor resolution in these circumstances.

US 2010/0153140 also discloses a high resolution mode of operation in which the ions are driven against a helical potential barrier such that the ions follow a helical path through the drift tube and separate along this helical path. The electric field along the device must be increased for a spiral path in order to maintain or improve the resolution of the device, as compared to an axial ion path, because the spiral path is longer. Although the field in the helical separation direction may be below the high field limit, the axial component of the field may exceed the high field limit, leading to changes in the ion mobility of different species. Furthermore, if the ions are evenly distributed annularly around the storage section, then when the ions are axially pulsed into the drift tube, ions from different annular starting positions will meet the helical potential barrier at different positions along the axis of the device. This causes a dramatic increase in the initial spatial spread of the ions and may have a severe impact on the attainable resolution from the device.

The ions are preferably randomly distributed around the circumference of the ion trap and/or around the ion guide.

The method preferably comprises confining ions axially and/or radially within said annular or co-axial ion trap.

Said annular or co-axial ion trap preferably comprises a plurality of first electrodes and said method preferably further comprises applying an RF or AC voltage to said first electrodes in order to confine ions radially within said annular or co-axial ion trap.

The ions are preferably radially confined between inner and outer electrodes in the annular or co-axial ion trap and/or the ion guide, and RF or AC potentials are preferably applied to said inner and outer electrodes in order to radially confine said ions.

The ions are preferably radially confined between inner and outer electrodes in the annular or co-axial ion trap and/or the ion guide, and each of the inner and outer electrodes preferably comprises a plurality of axially separated or segmented electrodes. Axially adjacent electrodes may be supplied with different phases of an RF voltage supply, preferably opposite phases.

The method may further comprise applying or maintaining a quadratic DC potential or other DC potential well along a longitudinal axial direction of said annular or co-axial ion trap in order to confine ions axially within said annular or co-axial ion trap.

As described above, the ions may be radially confined between inner and outer electrodes in the annular or co-axial ion trap, and each of the inner and outer electrodes may comprise a plurality of axially separated or segmented electrodes. Different DC potentials may be applied to these axially separated or segmented electrodes so as to form the quadratic DC potential or other DC potential well along a longitudinal axial direction.

The method preferably comprises confining ions within a toroidal ion trapping region within said annular or co-axial ion trap.

The method preferably comprises collisionally cooling ions and/or reducing the kinetic energy of ions within said annular or co-axial ion trap.

The step of axially ejecting at least some of said ions may comprise: (i) reducing the amplitude or removing an axial DC and/or RF potential barrier between said annular or co-axial ion trap and said annular ion guide; and/or (ii) reducing or altering the amplitude of a DC and/or RF voltage; and/or (iii) lowering, removing or altering a DC potential well or a pseudo-potential well; and/or (iv) changing a DC potential well to an extractive DC potential.

The step of axially ejecting at least some of said ions may comprise pulsing a DC electric field, preferably such that ions are pulsed out of the annular or co-axial ion trap and axially along said annular ion guide.

The step of axially ejecting at least some of said ions may comprise applying one or more transient DC voltages or voltage waveforms to said annular or co-axial ion trap. Preferably, the annular or co-axial ion trap comprises a series of axially segmented or separated electrodes and the step of applying one or more transient DC voltages or voltage waveforms comprises applying one or more DC voltages or voltage waveforms to successive ones of the electrodes such that a potential barrier is formed by the DC voltage that travels along the ion trap so as to drive the ions along and out of the ion trap.

The annular or co-axial ion trap has a first radius r1 and said annular ion guide has a second radius r2, wherein either r1>r2, r1=r2 or r1<r2.

The annular ion guide preferably comprises an ion mobility spectrometer or separator and the ions are separated according to their ion mobility as they pass along the ion guide. The ion guide preferably comprises a gas and the ions may be driven through the gas such that the ions separate according to their ion mobility through the gas. The ions may be pulsed into the ion mobility spectrometer or separator, may travel therethrough and may then be detected. The time between any given ion being pulsed into the spectrometer or separator and being detected may be used to determine the ion mobility of the ion.

The method may further comprise applying one or more transient DC voltages to said annular ion guide in order to urge ions along the axial length of said annular ion guide. Preferably, the ion guide comprises a series of axially segmented or separated electrodes and the step of applying one or more transient DC voltages to said ion guide comprises applying one or more DC voltages to successive ones of the electrodes such that a potential barrier is formed by the DC voltage that travels along the ion guide so as to drive the ions along the ion guide.

The method may comprise applying one or more static DC voltages to said annular ion guide, or a static potential difference along at least a portion of the ion guide, in order to urge ions along the axial length of said annular ion guide.

The method may comprise causing ions to be tunneled, funneled or otherwise focused towards an end of said annular ion guide.

A first end of said annular ion guide proximal to said annular or co-axial ion trap preferably has an annular ion confining region in cross-section and a second distal end of said ion guide may have a non-annular, circular, rectangular or other ion confining region in cross-section. The electrodes forming the ion guide are preferably arranged and configured such that ions are transmitted from the annular first end of the ion guide to the second end that has a non-annular, circular, rectangular or other shaped cross-section.

The method may comprise transferring ions from said annular ion guide into an ion tunnel ion guide, an ion funnel ion guide or a multipole rod set ion guide.

The method may comprise applying one or more DC voltages or potentials to one or more portions of said annular ion guide in order to cause ions to circumferentially redistribute and form a circumferentially compressed ion beam.

The method may comprise applying one or more voltages to at least a portion of said ion guide so as to force ions circumferentially around the ion guide into an arcuate section of the ion guide that extends over only a portion of the circumference of the ion guide. Said at least a portion of the ion guide is preferably the end of the ion guide opposite to the end that is proximal to the ion trap. The ions are preferably compressed into the arcuate section of the ion guide and are then transferred into a downstream device, such as a downstream ion guide, analyser or detector. By compressing the ions into the arcuate section at the end of the ion guide the ions are able to be more efficiently transferred into a downstream device having a non-annular cross-section for receiving the ions. The ions are preferably compressed into the arcuate section only at the end of the ion guide. The arcuate section of the ion guide preferably extends over only <75%, <50%, <30%, <20%, or <10% of the circumference of the ion guide.

The ion guide preferably comprises one or more electrodes arranged circumferentially around the axis of the ion guide, and wherein one or more voltages are applied to these electrodes so as to drive ions circumferentially around the ion guide into the arcuate section.

A plurality of electrodes are preferably arranged circumferentially around the axis of the ion guide and one or more voltages are applied to these electrodes so as to drive ions circumferentially around the ion guide into the arcuate section; and/or an electrode having a resistive coating may be arranged circumferentially around the axis of the ion guide and one or more voltages may be applied to the electrode so as to drive ions circumferentially around the ion guide into the arcuate section.

Preferably, the ions are radially confined in an annular region of the ion guide between inner and outer electrodes. Preferably, a plurality of the inner electrodes are arranged circumferentially around the axis of the ion guide and/or a plurality of the outer electrodes are arranged circumferentially around the axis of the ion guide. Voltages are applied to one or both of these inner and outer electrodes so as to drive ions circumferentially around the ion guide into the arcuate section.

The one or more voltages applied to the electrodes so as to drive ions into the arcuate section are preferably DC voltages, although may be RF pseudo-potentials.

The method may comprise focusing or compressing ions in a focusing region of the ion guide, wherein the focusing region is maintained at a reduced pressure relative to a portion of said annular ion guide proximal to said ion trap. The region in which ions are compressed into the arcuate section may be maintained at said reduced pressure.

A portion of said annular ion guide preferably comprises circumferentially segmented inner electrodes and/or circumferentially segmented outer electrodes and said method may comprise focusing ions, preferably into an arcuate section of the ion guide, by applying different DC potentials and/or different RF pseudo-potentials to said segmented inner electrodes and/or said segmented outer electrodes.

The method may comprise applying an angled or inclined DC potential or DC electric field to a portion of said annular ion guide in order to confine ions to a portion of the annular ion guiding volume of said annular ion guide.

The method may comprise applying an axial potential barrier around only part of the circumference of the ion guide such that ions cannot pass axially along the ion guide at the circumferential regions at which the barrier is located and ions can pass axially along the ion guide through an arcuate section of the ion guide where the barrier is not located.

The potential barrier preferably extends at an angle between a direction parallel to the longitudinal axis of the ion guide and a direction perpendicular to said axis, such that as the ions move axially along the ion guide they are forced circumferentially around the ion guide by the barrier into the arcuate section.

The barrier is preferably formed by applying DC potentials to electrodes forming the ion guide. As described above, the electrodes of the ion guide may be segmented circumferentially and/or axially and different potentials may be applied to these electrodes so as to form the barrier. Alternatively, AC or RF potentials may be applied to the electrodes so as to form the barrier.

The annular or co-axial ion trap preferably comprises a plurality of inner electrodes and a plurality of outer electrodes and an annular or co-axial ion trapping region between said inner and outer electrodes. Alternatively, or additionally, the annular ion guide preferably comprises a plurality of inner electrodes and a plurality of outer electrodes and an annular ion guiding region between said inner and outer electrodes.

The annular ion guide may comprise a plurality of inner electrodes and a plurality of outer electrodes and an annular ion guiding region between said inner and outer electrodes, wherein the radius of the annular ion guiding region decreases and/or increases in a direction from the end of the ion guide proximate to the ion trap to the opposite end of the ion guide.

The radii of the plurality of inner and outer electrodes forming said annular ion guide preferably progressively reduce along the axial length of the annular ion guide so as to form the ion guiding region of decreasing radius. Alternatively, the radii of the plurality of inner and outer electrodes forming said annular ion guide preferably progressively increase along the axial length of the annular ion guide so as to form the ion guiding region of increasing radius.

The outer radius of the annular ion guiding region within said annular ion guide may progressively taper or reduce.

The method may comprise maintaining said annular or co-axial ion trap at a first pressure p1 and maintaining said annular ion guide at second pressure p2, wherein p1>p2, p1=p2 or p1<p2.

The method may comprise injecting ions axially and/or tangentially into said annular or co-axial ion trap.

The method preferably comprises introducing ions into the ion trap along the longitudinal axis of the ion trap.

The ions are preferably driven through the ion guide by an electric field aligned in the axial direction of the ion guide, preferably wherein the field has a component only in the axial direction and not in the radial direction.

The present invention also provides a mass and/or ion mobility spectrometer comprising:

an annular or co-axial ion trap arranged and adapted to trap ions;

an annular ion guide; and a control system arranged and adapted:

(i) to trap ions in said annular or co-axial ion trap, wherein ions trapped in the ion trap are distributed around the entire circumference of the annular or co-axial ion trap; and (ii) to cause at least some ions within said annular or co-axial ion trap to be axially ejected from said annular or co-axial ion trap into said annular ion guide, wherein as the ions travel along at least a portion of the length of the ion guide their motion around the circumference of the annular ion guide is unrestricted, and wherein the ions separate axially as they travel along the ion guide;

wherein the electrode configuration of the spectrometer is arranged and configured to convert the ions from an ion beam having an annular shaped cross section to an ion beam having a non-annular shaped cross-section.

The spectrometer is preferably arranged and configured to perform any one of the methods described herein.

The annular or co-axial ion trap is preferably arranged and adapted to confine ions axially and/or radially within said annular or co-axial ion trap.

The annular or co-axial ion trap preferably comprises a plurality of first electrodes and said mass spectrometer is preferably arranged and adapted to apply an RF or AC voltage to said first electrodes in order to confine ions radially within said annular or co-axial ion trap.

The spectrometer is preferably configured to confine ions within a toroidal ion trapping region within said annular or co-axial ion trap.

The annular or co-axial ion trap is preferably arranged and adapted to collisionally cool ions and/or reduce the kinetic energy of ions within said annular or co-axial ion trap.

The spectrometer is preferably may comprise a device arranged and adapted to apply or maintain a quadratic DC potential or other DC potential well along an axial direction of said annular or co-axial ion trap in order to confine ions axially within said annular or co-axial ion trap.

The control system may be arranged and adapted to cause ions to be axially ejected from said annular or co-axial ion trap into said annular ion guide by: (i) reducing the amplitude or removing an axial DC and/or RF potential barrier between said annular or co-axial ion trap and said annular ion guide in order; and/or (ii) reducing or altering the amplitude of a DC and/or RF voltage; and/or (iii) lowering, removing or altering a DC potential well or a pseudo-potential well; and/or (iv) changing a DC potential well to an extractive DC potential.

The control system is preferably arranged and adapted to pulse a DC electric field in order to cause ions to be axially ejected from said annular or co-axial ion trap into said annular ion guide.

The control system may be arranged and adapted to apply one or more transient DC voltages or voltage waveforms to said annular or co-axial ion trap in order to cause ions to be axially ejected from said annular or co-axial ion trap into said annular ion guide.

The annular or co-axial ion trap has a first radius r1 and said annular ion guide has a second radius r2, wherein either r1>r2, r1=r2 or r1<r2.

The annular ion guide preferably comprises an ion mobility spectrometer or separator.

The spectrometer preferably comprises a device arranged and adapted to apply one or more transient DC voltages to said annular ion guide in order to urge ions along the axial length of said annular ion guide.

The spectrometer preferably comprises a device arranged and adapted to apply one or more static DC voltages to said annular ion guide in order to urge ions along the axial length of said annular ion guide.

The spectrometer may comprise a device arranged and adapted to cause ions to be tunneled, funneled or otherwise focused towards an end of said annular ion guide.

A first end of said annular ion guide proximal to said annular or co-axial ion trap may have an annular ion confining region in cross-section and a second distal end of said ion guide may have a non-annular, circular, rectangular or other ion confining region in cross-section.

The spectrometer may comprise a device arranged and adapted to transfer ions from said annular ion guide into an ion tunnel ion guide, an ion funnel ion guide or a multipole rod set ion guide.

The spectrometer may comprise a device arranged and adapted to apply one or more DC voltages or potentials to one or more portions of said annular ion guide in order to cause ions to redistribute and form a compressed ion beam.

The spectrometer may comprise a device arranged and adapted to reduce the pressure in an ion focusing region of said ion guide relative to a portion of said annular ion guide proximal to said annular or co-axial ion trap.

A portion of said annular ion guide preferably comprises one or more segmented inner electrodes and/or one or more segmented outer electrodes and said control system is preferably further arranged and adapted to focus ions by applying different DC potentials and/or different RF pseudo-potentials to said one or more segmented inner electrodes and/or said one or more segmented outer electrodes.

Said control system may be arranged and adapted to apply an angled or inclined DC potential or DC electric field to a portion of said annular ion guide in order to confine ions to a portion of the annular ion guiding volume of said annular ion guide.

Said annular or co-axial ion trap preferably comprises a plurality of inner electrodes and a plurality of outer electrodes and an annular or co-axial ion trapping region between said inner and outer electrodes.

Said annular ion guide preferably comprises a plurality of inner electrodes and a plurality of outer electrodes and an annular ion guiding region between said inner and outer electrodes.

The radius of the plurality of inner electrodes forming said annular ion guide may progressively reduce along the axial length of the annular ion guide.

The outer radius of the annular ion guiding volume within said annular ion guide may progressively taper or reduce.

The spectrometer may comprise a device arranged and adapted to maintain said annular or co-axial ion trap at a first pressure p1 and to maintain said annular ion guide at second pressure p2, wherein p1>p2, p1=p2 or p1<p2.

The spectrometer may comprise a device arranged and adapted to inject ions axially and/or tangentially into said annular or co-axial ion trap.

From a second aspect, the present invention provides a method of mass and/or ion mobility spectrometry comprising:

trapping ions in an annular or co-axial ion trap; and then axially ejecting at least some of said ions from said annular or co-axial ion trap into an annular ion guide.

The ions are preferably randomly distributed around the circumference of the ion trap and/or around the ion guide.

The method may comprise any one, or any combination of any two or more, of the features described above in relation to the first aspect of the present invention.

Ions trapped in the ion trap are preferably distributed around the entire circumference of the annular or co-axial ion trap.

As the ions travel along the ion guide their motion around the circumference of the annular ion guide is preferably unrestricted.

Ions preferably separate axially as they travel along the ion guide.

The method preferably comprises converting the ions from an ion beam having an annular shaped cross section to an ion beam having a non-annular shaped cross-section. The ion guide may be configured to convert the shape of the ion beam as it approaches the exit of the ion guide.

According to the second aspect of the present invention, there is also provided a mass and/or ion mobility spectrometer comprising:

an annular or co-axial ion trap arranged and adapted to trap ions;

an annular ion guide; and a control system arranged and adapted:

(i) to trap ions in said annular or co-axial ion trap;

(ii) to cause at least some ions within said annular or co-axial ion trap to be axially ejected from said annular or co-axial ion trap into said annular ion guide.

The spectrometer is preferably arranged and configured to perform any one, or any combination of any two or more, of the methods described herein.

For example, the electrodes of the ion guide may be arranged and configured so as to convert the shape of the ion beam as it approaches the exit of the ion guide from an annular shaped cross section to an ion beam having a non-annular shaped cross-section.

According to another aspect of the present invention there is provided a method of storing and injecting ions into a RF confined coaxial ion guide or coaxial ion trap comprising:

(a) storing ions in an annular volume comprising a toroidal ion trap or ion trapping region in which ions are randomly distributed;

(b) cooling or reducing the kinetic energy of the population of stored ions by collisions with buffer gas; and (c) ejecting the stored ions as a torus into a co-axial geometry ion guide.

The method may comprise any one, or any combination of any two or more, of the features described herein in respect of the first aspect of the present invention.

The toroidal ion trap is preferably part of the same structure as the coaxial ion guide.

The coaxial ion guide may comprise an ion mobility spectrometer or separator ("IMS") separation device.

Ejection may be achieved by rapid application of a pulsed DC acceleration field.

Ejection may be achieved by application of a travelling DC wave or one or more transient DC voltage waves.

According to an embodiment the spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may further comprise either:

(i) a C-trap and an orbitrap (RTM) mass analyser comprising an outer barrel-like electrode and a coaxial inner spindle-like electrode, wherein in a first mode of operation ions are transmitted to the C-trap and are then injected into the orbitrap (RTM) mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the orbitrap (RTM) mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprises a device arranged and adapted to supply an AC or RF voltage to the electrodes. The AC or RF voltage preferably has an amplitude selected from the group consisting of: (i)<50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i)<100 kHz; (ii) 100-200 kHz;

(iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The preferred embodiment relates to an improved method of ion storage and injection of a pulse or packet of ions into a coaxial RF confined ion guide.

According to a preferred embodiment a toroidal ion trapping region of similar or the same radial dimensions to the coaxial ion guide may be provided to first trap and condition an ion population and then rapidly inject the resultant torus of ions into the ion guide. The trapped ions are preferably allowed to fill the entire toroidal volume.

The toroidal trapping geometry preferably maximises the space charge capacity available and conditions the ion population into a volume which is preferably suitable for direct injection into the coaxial ion guide.

In the preferred embodiment the coaxial RF confined ion guide preferably comprises an ion mobility spectrometer or separator in which ions are driven from an entrance to an exit end using either a DC electric field or one or more transient DC voltages or DC travelling voltage waves.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Figure 1:
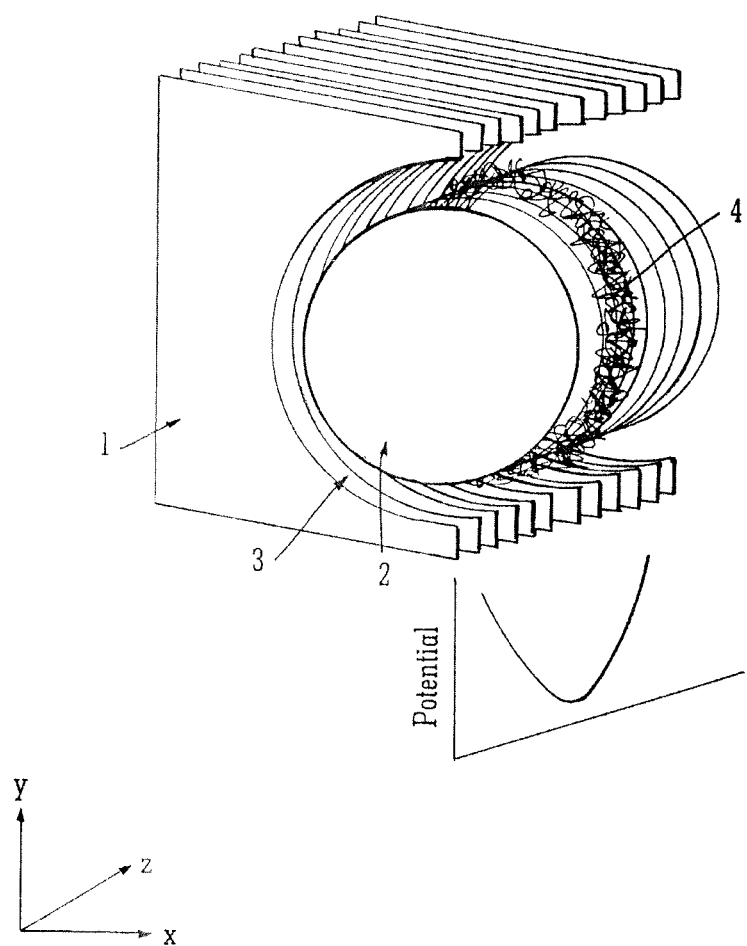
FIG. 1 shows a toroidal ion trapping region according to an embodiment of the present invention.

FIG. 1 shows a perspective view of a toroidal ion trapping region according to an embodiment of the present invention. The ion trap preferably comprises an inner set of axially separated electrodes 2 and an outer set of axially separated electrodes 1, which together define an annular ion trapping volume 3. Opposite phases of an RF frequency AC potential or voltage are preferably applied to axially alternate electrodes of the inner 2 and outer 1 electrode arrays so that an annular pseudo-potential trapping region is formed which acts to confine ions radially within the annular ion trapping volume 3.

A plot of electric potential as a function of distance along the axial length of the ion trap is also shown in FIG. 1 and shows a preferred form of an axial DC trapping potential which is preferably applied to a subset of electrodes on the inner array of electrodes 2 and the outer array of electrodes 1. Different DC potentials may be applied to different axial electrodes so as to form the trapping potential. The axial DC trapping potential provides a confining force on the ions in the axial direction. Ions may be injected from an external source into the trapping region 3 where they are preferably confined radially by a pseudo-potential well between the outer electrode 1 and the inner electrodes 2 and are also preferably confined axially by the DC potential well shown. The trapped ions are preferably reduced in kinetic energy (i.e. cooled) due to collisions with background gas. The could of ions 4 preferably takes up random positions around the annular or toroidal trapping volume as shown.

Figure 2:
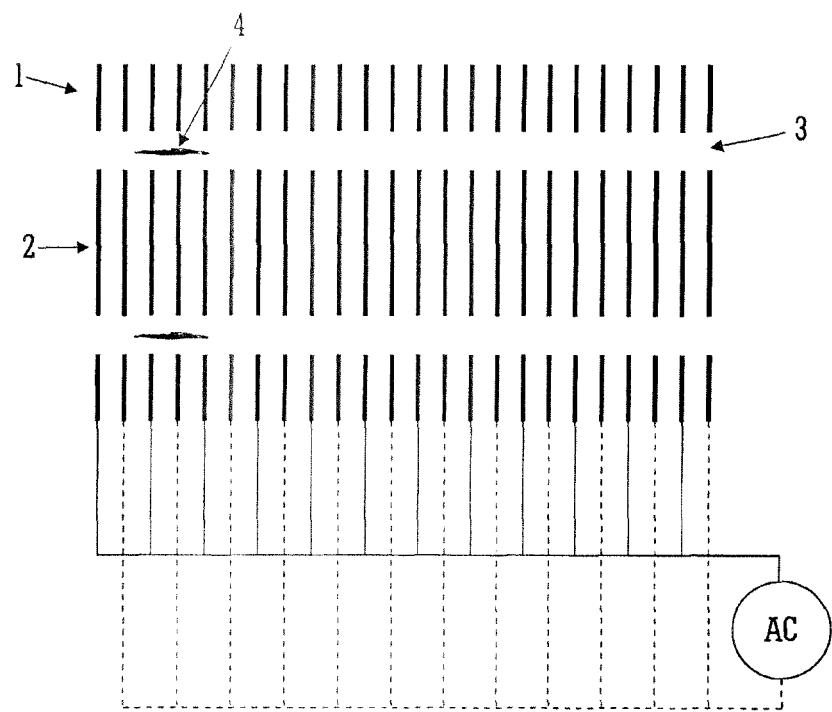
FIG. 2 shows a coaxial ion mobility spectrometer including an upstream toroidal ion trapping region with ions confined in the ion trapping region.
Figure 2:
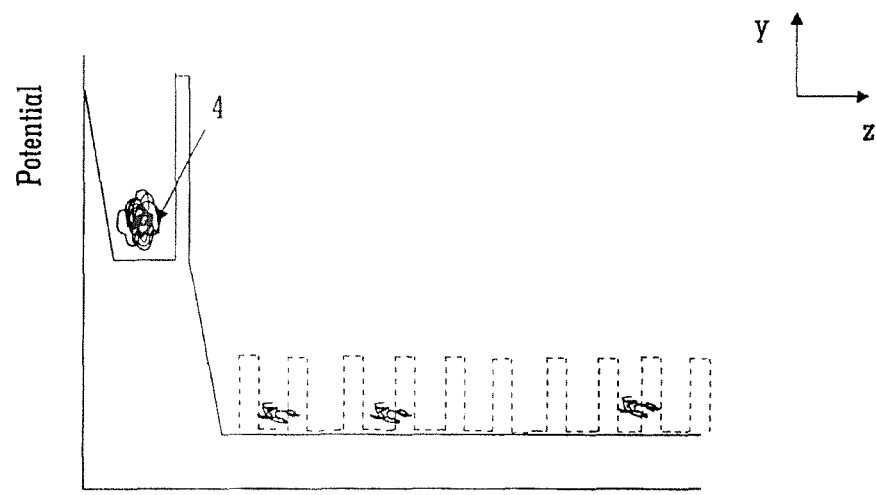

FIG. 2 shows an side view of an embodiment of the present invention comprising a coaxial ion mobility spectrometer or separator ("IMS") drift tube incorporating an upstream ion trapping region of the type shown in FIG. 1. The inner electrodes 2 and the outer electrodes 3 preferably provide ion confinement in the radial direction, as shown. This is achieved by applying RF voltages to the inner 2 and outer 3 electrodes. As described with reference to FIG. 1, ions are initially trapped in an toroidal trapping region at the entrance end of the device. When sufficient ions have been accumulated, the ions are pulsed out of the trapping region 4 and into the IMS drift tube. The ions traverse the drift tube and separate according to their ion mobilities. The ions may be detected after the have exited the drift tube and the duration of time between the pulsing of any given ion and its detection may be used to calculate the ion mobility of that ion. Preferably, ions are periodically pulsed from the trapping region 4 into the drift tube. Ions are preferably accumulated in the trapping region 4 in the period between any two sequential ion pulses, i.e. during the time that a previous ion population is traversing the ion guide.

A plot of electric potentials as a function of distance along the device is also shown in FIG. 2. The DC potentials are shown as solid lines. Ions enter the device and are preferably prevented from proceeding into the ion guiding region by application of a DC barrier. This causes ion to be trapped in ion trapping region 4. Ions from a previously trapped and released packet are preferably driven through the ion guide by application of a DC traveling wave or one or more transient DC voltages, shown as dotted lines, which drive the ions through the ion guide. These ions preferably separate and elute in order of their ion mobility.

Figure 3:
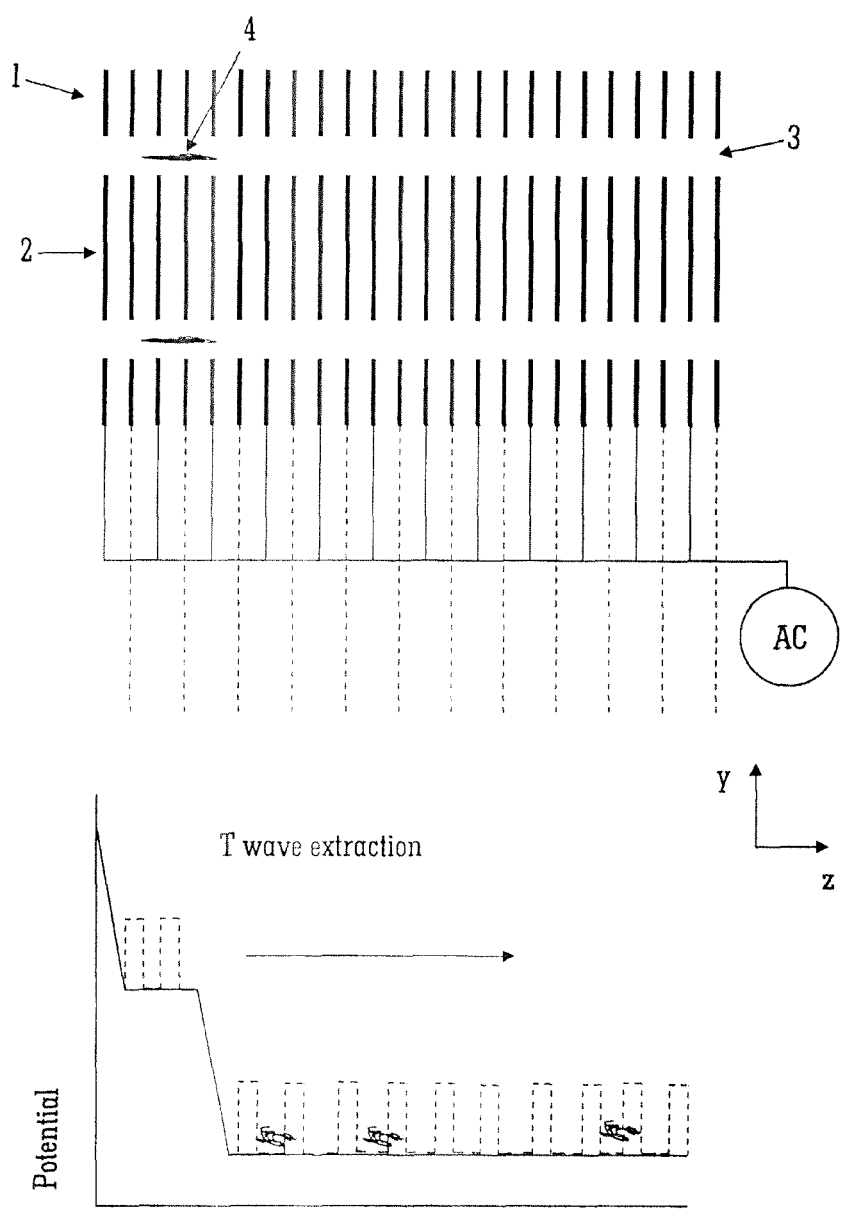
FIG. 3 shows a coaxial ion mobility spectrometer including a toroidal ion trapping region with ions being released from the ion trapping region into the ion mobility spectrometer.

FIG. 3 shows the same device as shown in FIG. 2 during a time period when an accumulated toroidal packet of ions is released into the ion guide. At this time the DC barrier of the trapping region 4 is reduced and a second DC transient wave (shown in dotted lines) is applied to the electrodes in the ion trapping region 4 in order to drive the packet of ions into the ion guide. The ions are then driven through the ion guide by a DC transient wave, as described in relation to FIG. 2. Once the ions have been pulsed into the ion guide the DC barrier is re-applied or restored and further ions are preferably accumulated. In this way a high charge density can be accommodated with a high duty cycle and high sensitivity.

According to an alternative embodiment, rather than be part of the same device at the same pressure, the trapping region 4 may comprise a separate device and may be held at a different pressure to the ion guide. A differential pumping aperture may be provided between the trapping region and the ion guide to enable this.

It is contemplated that the ions may be driven with a DC voltage gradient rather than a traveling DC voltage or one or more transient DC voltage waves.

Ions may be introduced into the trapping region 4 either tangentially with respect to circumference of the annular guide or alternatively along the longitudinal axis.

A method of focusing the ions at the exit of the device is also contemplated herein. The present invention introduces a packet of ions into and separates the ions within a coaxial ion guide, whilst maintaining a high space charge capacity by distributing ions within the entire annular volume. It is then often desired to couple the preferred device with other downstream devices. In particular, downstream devices may not have the same cross-sectional profile as the annular ion guide and therefore a method of interfacing a coaxial ion guide to these downstream devices is particularly advantageous. For example, once ions have been separated within the coaxial ion mobility spectrometer or separator device the separated ions may be directed towards a conventional ion guide with a substantially circular internal cross section.

One way of achieving this is to reduce the diameter of the internal annular cross section towards the exit of the device. For example, the diameter of the inner and outer electrodes may reduce towards the exit of the device. The diameter of the inner electrodes may reduce to substantially zero at the exit of the device.

An alternative method is disclosed, which does not depend on physically varying the dimension of the device. This method comprises applying a DC electric field gradient to a section of the coaxial ion guide acting in a substantially orthogonal direction to the primary direction of the ions travel such that ions in this section are redistributed to occupy a smaller arcuate trapping region. The DC electric field is preferably arranged such that ions are directed so that as they enter this region they are compressed into a volume or cross-sectional area suitable for subsequent transfer into a device having a non-coaxial geometry. Ions may be redistributed according to this technique so as to be places in two or more separate arcuate sections that are spaced circumferentially around the device. This may be useful, for example, to transmit ions to different downstream devices at the exit of the coaxial ion guide.

Figure 4:
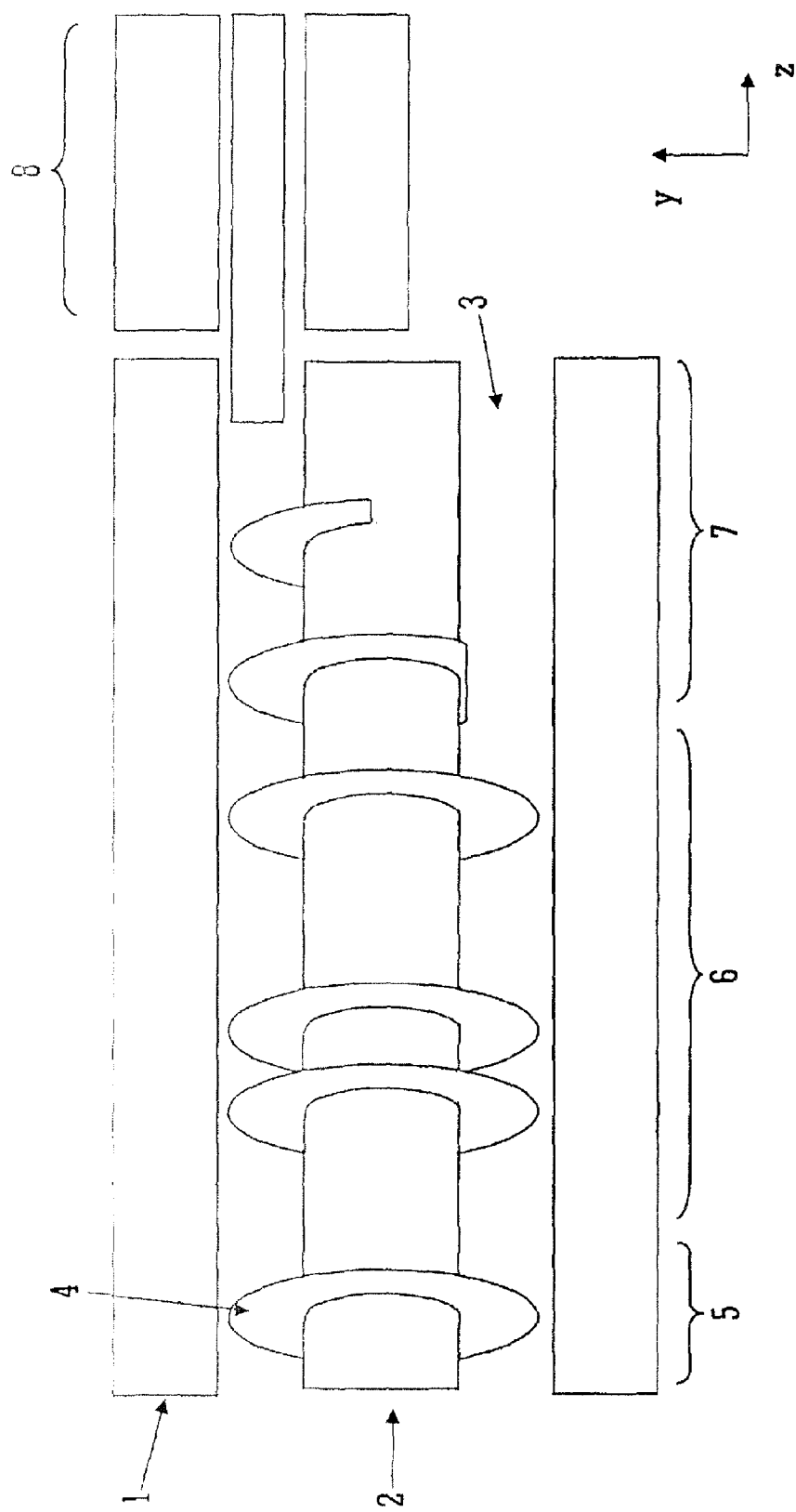
FIG. 4 shows an embodiment wherein ions are focused at the exit of the ion guide.

FIG. 4 shows a representation of a coaxial ion guide in the y,z plane with outer electrodes 1 and inner electrodes 2. The location of trapped ions 4 is shown in a toroidal trapping region 5 as previously described. Ions are preferably injected from the ion trapping region 5 into the ion guide or ion mobility spectrometer or separation region 6 and travel down the axial length of the ion guide in the z-direction. Throughout the trap 5 and the ion guide region 6 ions are substantially randomly distributed in the annular volume between the inner 2 and outer 1 electrodes. Ions then preferably enter a focusing region 7, wherein a DC potential is preferably applied in the y-direction so as to force ions from the lower part of the annular volume to the upper part. This redistribution occurs as the ions proceed down the z-axis of the device. The ions exit the device as a beam that has been compressed into an arcuate section of the device, rather than as a torus, and the ions can therefore be efficiently directed into a conventional ion guide 8.

As described above, ions may be urged in the z-direction by a DC field or a travelling wave.

The focusing region 7 may comprise part of the ion guide 6 and may be held at the same pressure, or may alternatively be a separate region separated by a differential pumping aperture that is held at a different pressure. If the regions are at different pressures, e.g. if the pressure in the IMS cell 6 is 2 mbar and the pressure in the focusing region 7 is 0.005 mbar, then ions in the focusing region 7 will move rapidly to a position in the desired region of the annular trapping volume without significant distortion of the IMS peak width or shape.

Figure 5:
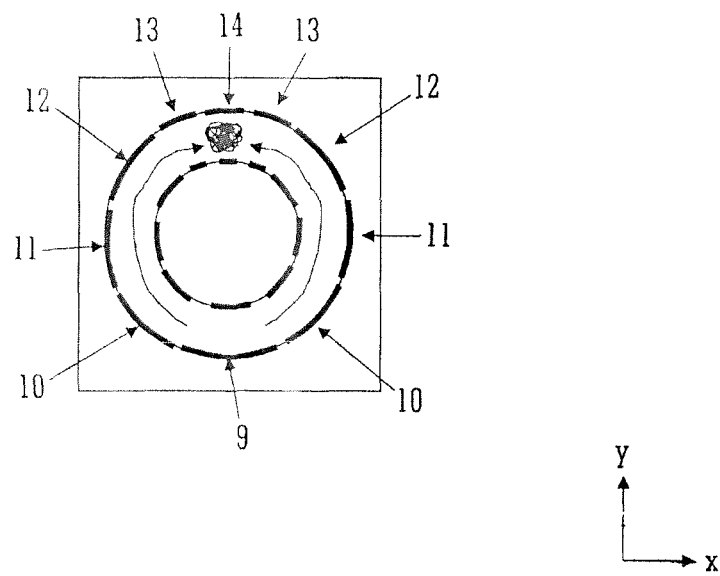
FIG. 5 shows a cross-sectional view of an embodiment arranged to focus ions at the exit of the ion guide.
Figure 5:
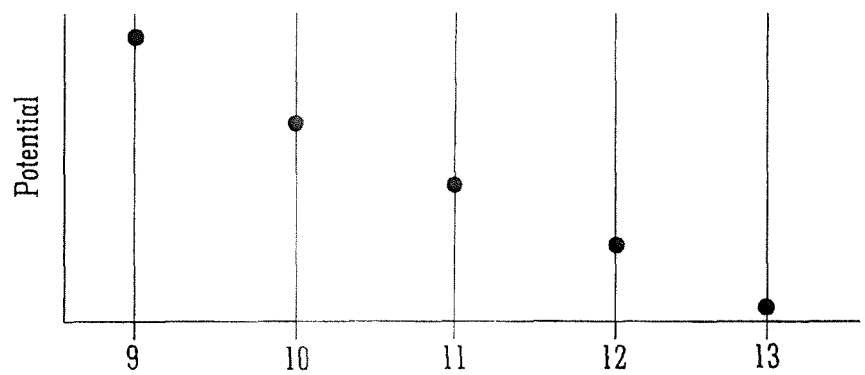

FIG. 5 shows a cross section through the focusing region 7 of FIG. 4 in the y,z plane. Each of the inner 2 and the outer electrodes 1 are preferably split into pairs of segments 9,10,11,12,13. The relative potential applied to each of these electrodes is indicated on the plot of potential versus segment number. It can be seen that the potentials applied to the segments decrease with segment number. In other words, the potentials applied to the segments progressively decrease around the circumference of the device from a maximum value on one side of the device to a minimum value on the opposite side of the device. This causes potential differences to be set up that force ions circumferentially around the device from the region of the maximum potential to the region of the minimum potential. The ions therefore take up the form of a compressed beam in an arcuate section of the device centered about the minimum potential. This arrangement results in a driving force that redistributes the ions to a small region of the annular volume of the ion guide, from which the ions can be easily extracted.

Other electrode arrangements are contemplated resulting in a similar effect. It is also possible to force ions into other areas or multiple areas of the annular trapping volume using this technique. Driving forces other than the DC potential gradients described above may be utilised. For example, RF voltages may be applied to the electrodes and the amplitudes of the RF voltages may be different on different segments resulting in a pseudo-potential driving force.

Figure 6:
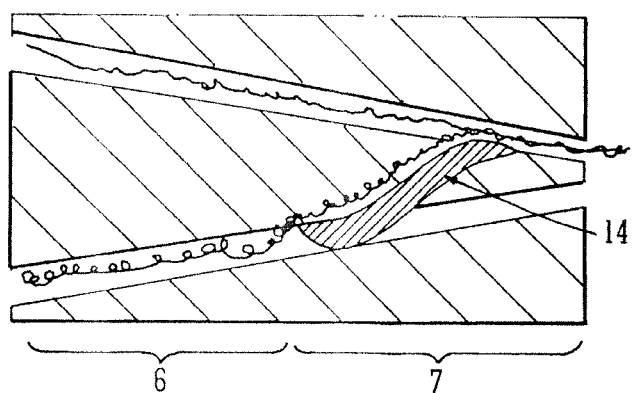
FIG. 6 shows another embodiment wherein the coaxial ion guide is tapered.

Another method for driving ions to the desired circumferential position in the device is to apply one or more potentials to the segmented electrodes in such a way that an angled DC barrier is formed within the focusing region 7 of the device. Ions which cannot overcome this barrier are urged to travel along the barrier by the axial driving force towards an extraction region. FIG. 6 shows a representation of such an embodiment and shows a coaxial ion guide 6 which is tapered to reduce the radius of the annular trapping region prior to the extraction region 7. A DC barrier 14 in the extraction region 7 is shown along with a representation of the ion path for illustration. Ions are preferably driven along this barrier to the exit. The barrier blocks the axial motion of the ions except for in the upper arcuate section of the device. As the ions are forced along the device, they ride up the barrier towards the upper arcuate section. The ions are then compressed into this upper arcuate section. As there is no barrier in the upper arcuate section the ions can then travel to the exit of the device in a compressed ion beam, which may be useful for subsequent extraction and transmission into another device.

Although the present invention has been described with reference to preferred embodiments, it will be understood by those skilled in the art that various changes in form and detail may be made without departing from the scope of the invention as set forth in the accompanying claims.

For example, although the annular ion guide has been described herein as forming an ion mobility spectrometer, the advantages of the present invention are also provided when the annular ion guide forms part of other types of devices. In particular, the configuration is also advantageous for avoiding space charge effects in other devices.

The invention claimed is:

1. A method of mass or ion mobility spectrometry comprising:

trapping ions in an annular or co-axial ion trap to establish trapped ions, wherein the trapped ions are distributed around the entire circumference of the annular or co-axial ion trap; and then axially ejecting at least some of said trapped ions, to establish ejected ions, from said annular or co-axial ion trap into an annular ion guide, wherein the ejected ions separate axially as the ejected ions travel along the ion guide, and wherein as the ejected ions travel along at least a portion of the length of the ion guide a motion of the ejected ions around the circumference of the annular ion guide is unrestricted; and then converting the ejected ions from an ion beam having an annular shaped cross section to an ion beam having a non-annular shaped cross-section.

2. A method as claimed in claim 1, wherein the trapped ions are randomly distributed around the circumference of the ion trap or the ejected ions are randomly distributed around the ion guide.

3. A method as claimed in claim 1, wherein the trapped ions are radially confined between inner and outer electrodes in the annular or co-axial ion trap and RF or AC potentials are applied to said inner and outer electrodes in order to radially confine said trapped ions or wherein the ejected ions are radially confined between inner and outer electrodes in the annular ion guide and RF or AC potentials are applied to said inner and outer electrodes in the annular ion guide in order to confine said ejected ions.

4. A method as claimed in claim 1, wherein the trapped ions are radially confined between inner and outer electrodes in the annular or co-axial ion trap and each of the inner and outer electrodes comprises a plurality of axially separated or segmented electrodes or wherein the ejected ions are radially confined between inner and outer electrodes in the annular ion guide and each of the inner and outer electrodes in the ion guide comprises a plurality of axially separated or segmented electrodes.

5. A method as claimed in claim 1, comprising applying or maintaining a quadratic DC potential or other DC potential well along a longitudinal axial direction of said annular or co-axial ion trap in order to confine ions axially within said annular or co-axial ion trap.

6. A method as claimed in claim 1, wherein said annular ion guide comprises an ion mobility spectrometer or separator and wherein the ejected ions are separated according to ion mobility as the ejected ions pass along the ion guide.

7. A method as claimed in claim 1, comprising applying one or more transient DC voltages to said annular ion guide in order to urge ions along the axial length of said annular ion guide; or comprising applying one or more static DC voltages to said annular ion guide, or a static potential difference along at least a portion of the ion guide, in order to urge ions along the axial length of said annular ion guide.

8. A method as claimed in claim 1, comprising causing the ejected ions to be tunneled, funneled or otherwise focused towards an end of said annular ion guide, preferably after the ejected ions have separated axially.

9. A method as claimed in claim 1, wherein a first end of said annular ion guide proximal to said annular or co-axial ion trap has an annular ion confining region in cross-section and wherein a second distal end of said ion guide has a non-annular, circular, rectangular or other ion confining region in cross-section.

10. A method as claimed in claim 1, comprising applying one or more DC voltages or potentials to one or more portions of said annular ion guide in order to cause ions to circumferentially redistribute and form a circumferentially compressed ion beam.

11. A method as claimed in claim 1, comprising applying one or more voltages to at least a portion of said ion guide so as to force ions circumferentially around the ion guide into an arcuate section of the ion guide that extends over only a portion of the circumference of the ion guide.

12. A method as claimed in claim 11, wherein the ion guide comprises one or more electrodes arranged circumferentially around the axis of the ion guide, and wherein one or more voltages are applied to these electrodes so as to drive ions circumferentially around the ion guide into the arcuate section.

13. A method as claimed in claim 1, comprising focusing or compressing ions in a focusing region of the ion guide, wherein the focusing region is maintained at a reduced pressure relative to a portion of said annular ion guide proximal to said ion trap.

14. A method as claimed in claim 1, wherein a portion of said annular ion guide comprises circumferentially segmented inner electrodes or circumferentially segmented outer electrodes and wherein said method further comprises focusing ions, into an arcuate section of the ion guide, by applying different DC potentials or different RF pseudo-potentials to said segmented inner electrodes or said segmented outer electrodes.

15. A method as claimed in claim 1, comprising applying an axial potential barrier at circumferential regions of the ion guide such that ions cannot pass axially along the ion guide at the circumferential regions at which the barrier is located and ions can pass axially along the ion guide through an arcuate section of the ion guide where the barrier is not located.

16. A method as claimed in claim 15, wherein the potential barrier is extends at an angle between a direction parallel to the longitudinal axis of the ion guide and a direction perpendicular to said axis, such that as the ions move axially along the ion guide the ions are forced circumferentially around the ion guide by the barrier into the arcuate section.

17. A method as claimed in claim 1, comprising introducing the ions into the ion trap along the longitudinal axis of the ion trap.

18. A method as claimed in claim 1, comprising repeatedly performing a cycle of operation, wherein each cycle of operation comprises:

axially ejecting trapped ions from said ion trap into said ion guide, to establish axially ejected ions; and accumulating and trapping different ions in the ion trap whilst the axially ejected ions are being separated in the ion guide.

19. A mass or ion mobility spectrometer comprising:

an annular or co-axial ion trap arranged and adapted to trap ions;

an annular ion guide; and a control system arranged and adapted:

(i) to trap ions in said annular or co-axial ion trap, wherein ions trapped in the ion trap are distributed around the entire circumference of the annular or co-axial ion trap; and (ii) to cause at least some ions within said annular or co-axial ion trap to be axially ejected from said annular or co-axial ion trap into said annular ion guide, to establish elected ions wherein as the ejected ions travel along at least a portion of the length of the ion guide the motion of the ejected ions around the circumference of the annular ion guide is unrestricted, and wherein the ejected ions separate axially as ejected travel along the ion guide;

wherein an electrode configuration of the spectrometer is arranged and configured to convert the ejected ions from an ion beam having an annular shaped cross section to an ion beam having a non-annular shaped cross-section.

20. A method of mass or ion mobility spectrometry comprising:

trapping ions in an annular or co-axial ion trap; and then axially ejecting at least some of said ions from said annular or co-axial ion trap into an annular ion guide.

* * * * *